(12) United States Patent
Watts

(10) Patent No.: US 9,655,661 B1
(45) Date of Patent: May 23, 2017

(54) CANNULATED ORTHOPEDIC SCREW AND METHOD OF REDUCING AND FIXING A FRACTURE OF THE LATERAL MALLEOLUS

(71) Applicant: Hugh Boyd Watts, Salisbury, NC (US)

(72) Inventor: Hugh Boyd Watts, Salisbury, NC (US)

( * ) Notice: Subject to any disclaimer, the term of this patent is extended or adjusted under 35 U.S.C. 154(b) by 0 days.

(21) Appl. No.: 15/198,467

(22) Filed: Jun. 30, 2016

(51) Int. Cl.
*A61B 17/72* (2006.01)
*A61B 17/88* (2006.01)

(52) U.S. Cl.
CPC ...... *A61B 17/7291* (2013.01); *A61B 17/8897* (2013.01)

(58) Field of Classification Search
CPC . A61B 17/72; A61B 17/7291; A61B 17/7208; A61B 17/7225; A61B 17/7233; A61B 17/84; A61B 17/846; A61B 17/848; A61B 17/86; A61B 17/864; A61B 17/8645
See application file for complete search history.

(56) References Cited

U.S. PATENT DOCUMENTS

| | | | | | |
|---|---|---|---|---|---|
| 4,463,753 | A * | 8/1984 | Gustilo | ................ | A61B 17/863 411/386 |
| 5,248,313 | A * | 9/1993 | Greene | .............. | A61B 17/1725 606/60 |
| 7,963,966 | B2 * | 6/2011 | Cole | .................... | A61B 17/683 606/62 |
| 8,092,505 | B2 * | 1/2012 | Sommers | ............... | A61B 17/68 606/317 |
| 2003/0045881 | A1 * | 3/2003 | Barouk | ................ | A61B 17/863 606/304 |
| 2005/0101961 | A1 * | 5/2005 | Huebner | ............ | A61B 17/8605 606/304 |
| 2005/0107791 | A1 * | 5/2005 | Manderson | ............ | A61B 17/68 606/62 |
| 2007/0010819 | A1 * | 1/2007 | Johnstone | .......... | A61B 17/1735 606/291 |
| 2007/0282341 | A1 * | 12/2007 | Hes | ....................... | A61B 17/863 606/328 |
| 2009/0062797 | A1 * | 3/2009 | Huebner | ............ | A61B 17/1739 606/62 |
| 2010/0211113 | A1 * | 8/2010 | Olson | ................ | A61B 17/8625 606/301 |
| 2013/0144344 | A1 * | 6/2013 | Giancola | ............ | A61B 17/7098 606/304 |
| 2013/0245626 | A1 * | 9/2013 | Lavi | ........................ | A61B 17/72 606/62 |
| 2016/0030097 | A1 * | 2/2016 | Mildner | ............... | A61B 17/863 606/304 |

FOREIGN PATENT DOCUMENTS

| | | | | |
|---|---|---|---|---|
| CH | EP 0682917 | A1 * | 11/1995 | ......... A61B 17/1757 |
| DE | 2558446 | A1 * | 7/1976 | ............... A61F 2/36 |

OTHER PUBLICATIONS

Translation of EP 0682917.*
Translation of DE 2558446.*

* cited by examiner

*Primary Examiner* — Lynnsy Summitt
(74) *Attorney, Agent, or Firm* — Shumaker, Loop & Kendrick, LLP

(57) ABSTRACT

An orthopedic screw that includes a screw shaft having a predetermined length with a cannula extending through the length of the shaft. The shaft includes a first, relatively large outside diameter proximal segment; and a second, relatively small outside diameter threaded distal segment adjacent the proximal segment.

5 Claims, 2 Drawing Sheets

Figure 1:
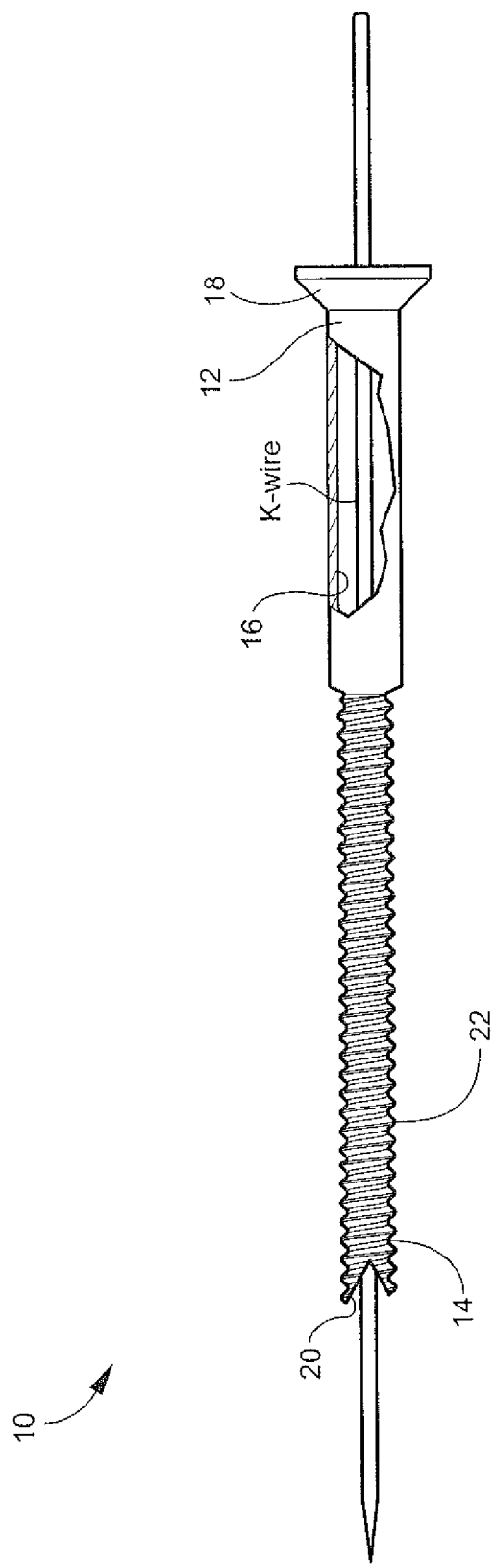

CANNULATED ORTHOPEDIC SCREW AND METHOD OF REDUCING AND FIXING A FRACTURE OF THE LATERAL MALLEOLUS

TECHNICAL FIELD AND BACKGROUND OF THE INVENTION

This invention relates to a cannulated orthopedic screw having particular application in the distal proximal fixation of lateral malleolus fractures. The ankle joint is made up of three bones coming together. The tibia, which is the main bone of the lower leg, makes up the medial or inside anklebone. The fibula is a smaller bone that parallels the tibia in the lower leg and makes up the lateral or outside anklebone. The distal ends of both the tibia and fibula are known as the malleoli (singular is malleolus). Together, they form an arch that sits on top of the talus, one of the bones in the foot. These three bones (tibia, fibula, and talus) make up the bony elements of the ankle joint. A fibrous membrane called the joint capsule, lined with a smoother layer called the synovium, encases the joint architecture. The joint capsule contains the synovial fluid produced by the synovium. The synovial fluid allows for smooth movement of the joint surfaces. The ankle joint is stabilized by several ligaments, which are fibers that hold these bones in place.

Ankle fractures occur when the malleoli are broken. These fractures are very common. Ankle fractures can happen after falls, car accidents or twisting of the ankle. One, two or all three malleoli can be broken.

Fixation of a lateral malleolus fracture has evolved over many years. Initial treatment was a closed reduction with a cast or splint. Later practices included the use of rush rods, screws and simple plates. More recent treatments have included the use of stronger and wider plates with screws or locking plates.

Patients are instructed in non-weight bearing or minimal weight bearing activities based on the fracture pattern, bone density, weight of the patient, mental condition and level of fixation obtained at surgery. Good accurate fixation in young patients is essential for good long-term results but even with accurate fixation, some patients develop non-union or articular cartilage damage and require some type of replacement later due to the cartilage damage or infection.

Older patients with osteopenia and more physical problems present a different problem. Most fixations of the lateral malleolus if displaced require open striping of tissue from the distal fibula and plate fixation with multiple cortical and cancellous screws. A distal to proximal fixation of the lateral malleolus offers another way to reduce and stabilize the lateral malleolus. Such a procedure would alleviate the need for open fixation with plates and screws especially in older patients with Alzheimer's, osteoporosis, and other medical conditions. This would permit a quicker fixation with a retrograde screw from the distal tip of the lateral malleolus up the canal of the proximal fibula. At present, there is no screw available that permits larger distal fixation and smaller proximal fixation.

SUMMARY OF THE INVENTION

It is therefore an object of the present invention to provide an orthopedic screw for distal fibula fixation.

It is another object of the invention to provide an orthopedic screw for distal fibula fixation which can be applied to the patient in less time, resulting in a saving in Operating Room time.

It is another object of the invention to provide an orthopedic screw for distal fibula fixation that results in faster healing due to elimination of the need to strip soft tissue from the fibula.

It is another object of the invention to provide an orthopedic screw for distal fibula fixation, which permits a smaller skin incision and less chance of infection.

It is another object of the invention to provide an orthopedic screw for distal fibula fixation which results in less chance of metal removal at a later date with the need for additional surgery.

It is another object of the invention to provide an orthopedic screw for distal fibula fixation that results in less chance of loss of reduction if the patient falls during the post-op period.

It is another object of the invention to provide an orthopedic screw for distal fibula fixation that results in better reduction and fixation when used on osteoporosis patients.

It is another object of the invention to provide an orthopedic screw for distal fibula fixation, which can in some cases based on physician judgment allow for earlier weight-bearing activities.

It is another object of the invention to provide an orthopedic screw for distal fibula fixation that is particularly suitable for Alzheimer patients. Because of the ability to allow the patient to bear weight on the fracture sooner, it reduces the possibility of further injury due to the inability of such patients to remember that they cannot place weight on the healing fracture.

These and other objects and advantages of the invention are achieved by providing an orthopedic screw that includes a screw shaft having a predetermined length with a cannula extending through the length of the shaft. The shaft includes a first, relatively large outside diameter proximal segment and a second, relatively small outside diameter threaded distal segment adjacent the proximal segment.

According to another embodiment of the invention, the proximal segment and the distal segment are unitary.

According to another embodiment of the invention, the proximal segment includes a flared end.

According to another embodiment of the invention, the cannula is adapted to receive a surgical wire therethrough.

According to another embodiment of the invention, the length of the screw is between 80 and 130 mm.

According to another embodiment of the invention, the outside diameter of the proximal segment is between 5.0 and 6.0 mm.

According to another embodiment of the invention, the outside diameter of the distal segment is between 4.0 and 4.5 mm.

According to another embodiment of the invention, an orthopedic screw is provided that includes a unitary screw shaft having a predetermined length and a cannula extending through the length of the shaft and adapted to receive a surgical wire therethrough. The unitary screw shaft includes a first, relatively large outside diameter proximal segment having a flared end and a second, relatively small outside diameter threaded distal segment adjacent the proximal segment.

According to another embodiment of the invention, a method of reducing and fixing a fracture of the lateral malleolus is provided that includes the steps of reducing the lateral malleolus of the fibula with the shaft of the fibula and forming a bore in the lateral malleolus and the shaft of the fibula. A surgical wire is inserted through the bore in the lateral malleolus and the shaft of the fibula. An orthopedic screw is inserted into and through the bore in the lateral malleolus and the shaft of the fibula using the surgical wire as a guide for movement of the orthopedic screw into a position where the lateral malleolus and the shaft of the fibula are joined in a fixed position. The orthopedic screw includes a screw shaft having a predetermined length and a cannula extending through the length of the shaft. The shaft includes a first, relatively large outside diameter proximal segment and a second, relatively small outside diameter threaded distal segment adjacent the proximal segment.

According to another embodiment of the invention, the surgical wire is removed from the cannula of the orthopedic screw after the lateral malleolus and the shaft of the fibula are joined in a fixed position.

BRIEF DESCRIPTION OF THE DRAWING FIGURES

Figure 2:
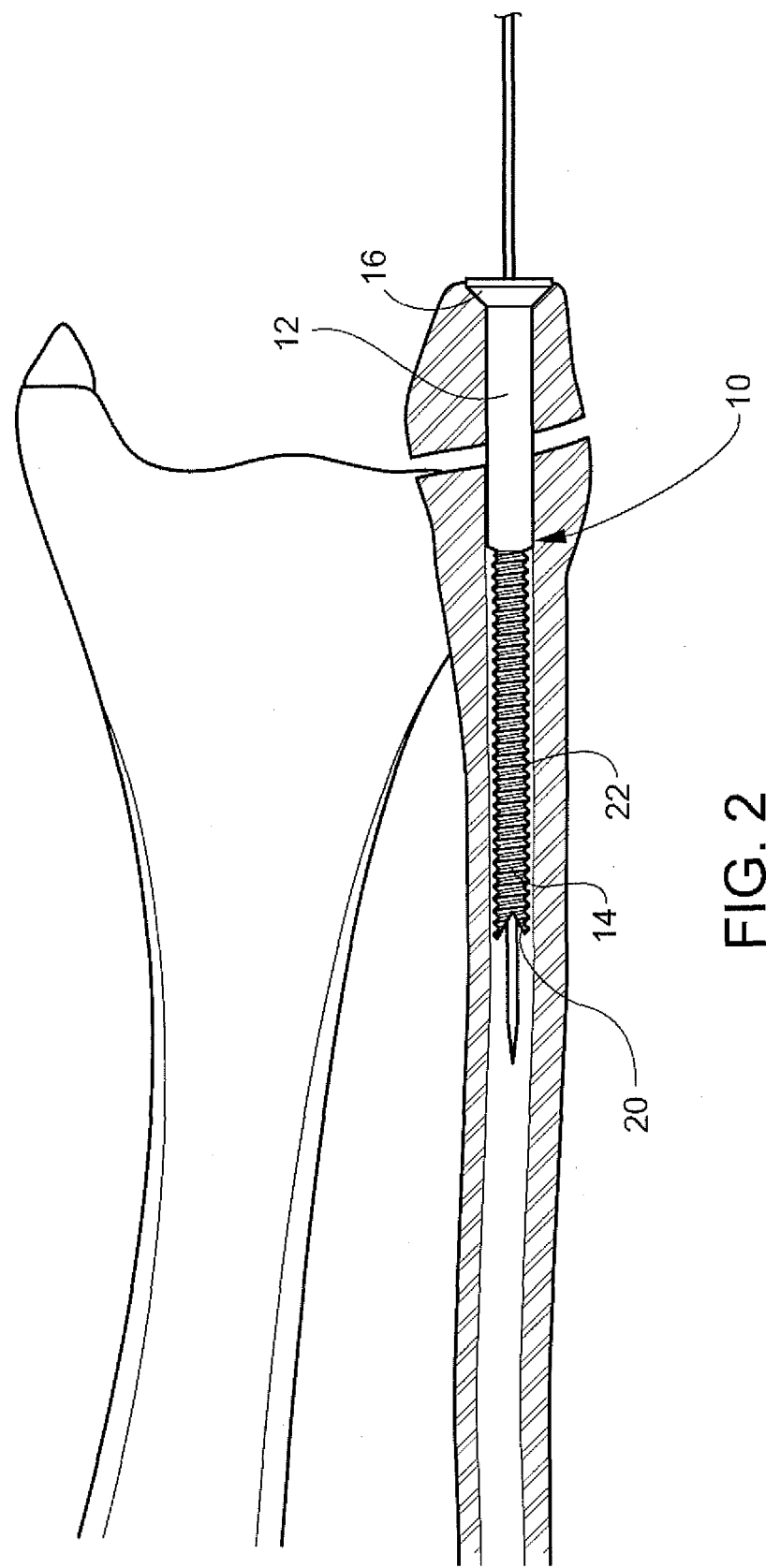

The present invention is best understood when the following detailed description of the invention is read with reference to the accompanying drawings, in which:

FIG. 1 is a side longitudinal elevation of an orthopedic screw in accordance with one preferred embodiment of the invention; and FIG. 2 is an environmental, partial cross-sectional elevation showing the orthopedic screw in position in a fractured, reduced fibula.

DETAILED DESCRIPTION OF THE PREFERRED EMBODIMENT

Referring now to the drawings, an orthopedic screw according to one preferred embodiment of the invention is shown at reference numeral 10. The screw 10 is fabricated of surgical grade steel. The screw 10 includes a relatively large outer diameter proximal segment 12 and a relatively small outer diameter distal segment 14. The relatively larger diameter of the proximal segment 12 provides enhanced medial and lateral stability to the fracture during healing. A cannula 16 extends through both segments 12 and 14. The proximal segment 12 includes a flared end 18 that facilitates guidance of a Kirschner wire ("K-wire") into and through the cannula 16 and out the remote end 20 of the distal segment 14. The diameter of the K-wire is selected based on the diameter of the cannula 16. The end 20 has a sharp, biting edge to facilitate passage of the screw 10 through the cortex of the lateral malleolus and the fibula. The distal segment 14 is provided with threads 22 to facilitate cortical purchase.

The cannula 16 permits guidance of the screw 10 on the K-wire, which can then remain in place or be removed after the screw 10 has been properly fixed in position.

Referring now to FIG. 2, a fracture of the lateral malleolus of the fibula is shown. The fracture is shown having been reduced in accordance with proper medical procedure with a screw 10 according to the invention. The relatively large diameter proximal segment 12 allows for medial and lateral stability of the reduced fracture, facilitating earlier weight-bearing activities of the patient. The narrower threaded distal segment 14 allows for adequate cortical purchase by the screw while preserving adequate thickness of the surrounding bone.

The dimensions set out below represent non-exclusive examples of appropriate sizes:

Overall length of screw 10—80, 90, 100, 110, 120 and 130 mm.

Outside diameter of proximal segment—5.0, 5.5, 6.0 mm.

Outside diameter of distal segment—4.0, 4.5 mm.

The cannula 16 allows for initial insertion of a K-wire to reduce the fracture and subsequent use of the K-wire as a guide as the screw 10 is inserted as shown in FIG. 2. Moreover, the screw can be fully or partially threaded.

A cannulated orthopedic screw according to the invention has been described with reference to specific embodiments and examples. Various details of the invention maybe changed without departing from the scope of the invention. Furthermore, the foregoing description of the preferred embodiments of the invention and best mode for practicing the invention are provided for the purpose of illustration only and not for the purpose of limitation, the invention being defined by the claims.

I claim:

1. An orthopedic screw for reducing a bone fracture, comprising:
   (a) a unitary, one-piece screw shaft having a predetermined length;
   (b) a cannula extending through an entire length of the shaft;
   (c) a terminal head having a constant slope that is integrally formed with and directly connected to a non-threaded proximal segment of the shaft; and
   (d) the shaft including:
      (i) the non-threaded proximal segment directly connected to a threaded distal segment;
      (ii) the non-threaded proximal segment being non-threaded throughout its entire length and having a predetermined outside diameter and the terminal head having an outside diameter greater than the outside diameter of the proximal segment for rotating the screw;
      (iii) the threaded distal segment being threaded throughout its entire length and having a non-tapered terminal end portion, the threaded distal segment having a predetermined maximum outside diameter smaller than a smallest outside diameter of the non-threaded proximal segment, the threads of the distal segment positioned on the screw and having a length comprising a majority of the length of the screw shaft, wherein the threads are adapted to be driven distally of the fracture such that further rotation of the screw reduces the fracture by tightening first and second bone fragments together; and
      (iv) the terminal end portion of the distal segment of the shaft including a sharp, biting end edge adapted to facilitate passage of the screw through a cortex of a lateral malleolus and fibula of a bone.

2. An orthopedic screw for reducing a bone fracture according to claim 1, wherein the cannula is adapted to receive a surgical wire therethrough.

3. An orthopedic screw for reducing a bone fracture according to claim 1, wherein the length of the screw is between 80 and 130 mm.

4. An orthopedic screw for reducing a bone fracture according to claim 1, wherein the outside diameter of the proximal segment is between 5.0 and 6.0 mm.

5. An orthopedic screw for reducing a bone fracture according to claim 1, wherein the outside diameter of the distal segment is between 4.0 and 4.5 mm.

* * * * *